Figure 4:
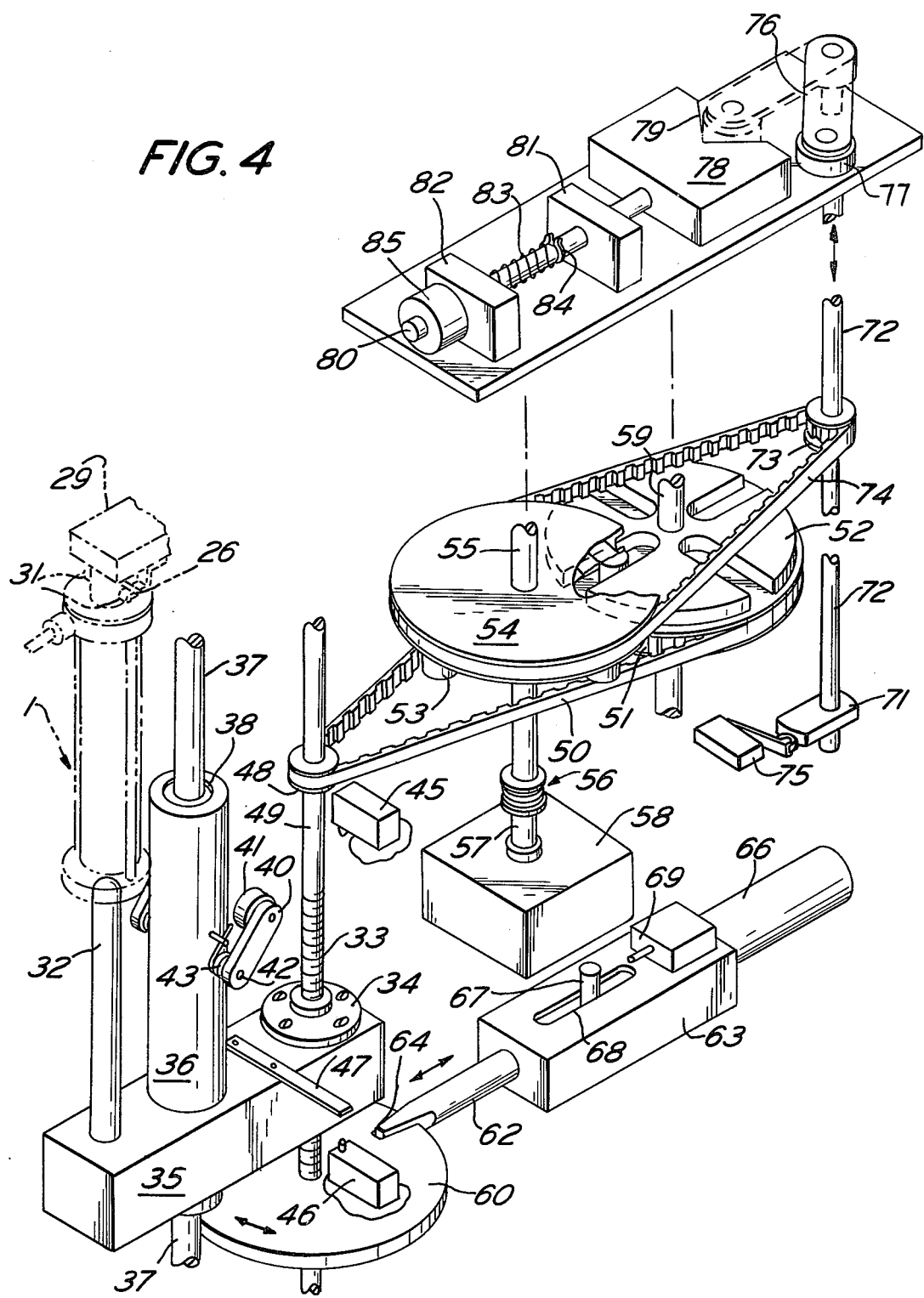

United States Patent [19]

Downings et al.

[11] 3,931,915

[45] Jan. 13, 1976

[54] LIQUID-CONTAINING CARTRIDGE AND A DEVICE FOR DISPENSING MEASURED AMOUNT OF LIQUID FROM SUCH A CARTRIDGE

[75] Inventors: Harvey T. Downings; Byron E. Sturgis, both of Huntsville, Ala.

[73] Assignee: Micromedic Systems, Inc., Horsham, Pa.

[22] Filed: Oct. 10, 1973

[21] Appl. No.: 405,226

[52] U.S. Cl. .................. 222/327; 92/199; 222/333; 222/390
[51] Int. Cl.² ........................................ G01F 11/02
[58] Field of Search .......... 222/327, 326, 333, 390, 222/60, 63, 380; 92/199

[56] References Cited
UNITED STATES PATENTS

| | | | |
|---|---|---|---|
| 1,027,251 | 5/1912 | Hill | 222/390 X |
| 1,232,076 | 7/1917 | Pettit | 222/390 |
| 1,259,474 | 3/1918 | Barr | 222/327 |
| 1,577,570 | 3/1926 | Egli | 92/199 X |
| 2,822,959 | 2/1958 | Soehnlen et al. | 222/327 |
| 3,390,815 | 7/1968 | Kavan et al. | 222/333 X |
| 3,419,051 | 12/1968 | Gustafson et al. | 222/390 X |
| 3,700,141 | 10/1972 | Cristiani | 222/333 X |

FOREIGN PATENTS OR APPLICATIONS

| | | | |
|---|---|---|---|
| 493,325 | 4/1954 | Italy | 222/386 |

Primary Examiner—Stanley H. Tollberg
Assistant Examiner—Hadd Lane

[57] ABSTRACT

The invention is concerned with a novel container for receiving a liquid material having a fitting at one end adapted to provide a discharge port for the liquid within the container and having at its other end a plunger or piston adapted to be moved within the inside wall of the container to discharge one or more predetermined "aliquots" or "doses" of liquid from the container through the port. The invention also comprises a novel device adapted to receive a liquid-containing cartridge or package of the type just mentioned and having means for coacting with the package to move the plunger within the container during dose-dispensing or -discharge in such a manner as to gradually accelerate movement of the plunger from a position of rest within the container through a maximum rate of motion and then gradually decelerate the motion of the plunger to a final position at the end of the dose-discharge. The device also comprises means for accurately predetermining or "measuring" the amount of liquid discharged during each individual movement of the plunger. The device may comprise means for repeatedly actuating the piston with an accelerating-decelerating movement to discharge a plurality of measured samples repeatedly under non-spurt and non-splash conditions.

17 Claims, 7 Drawing Figures

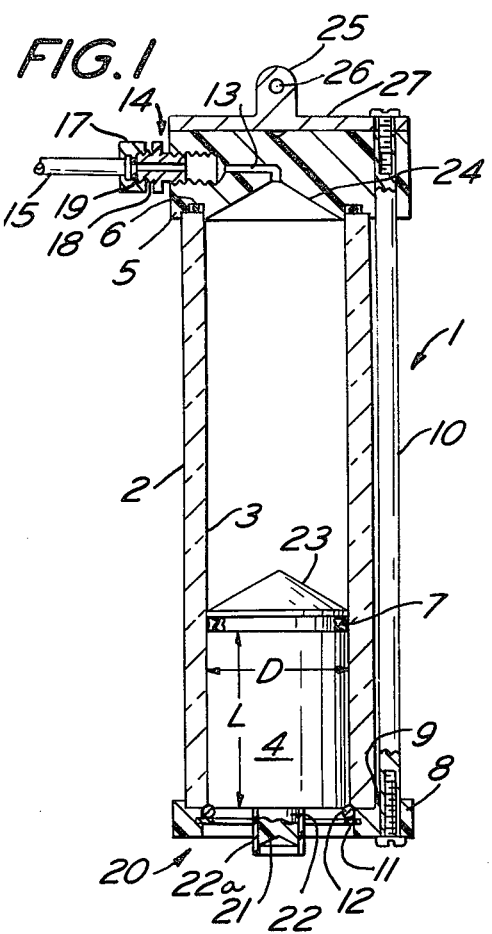
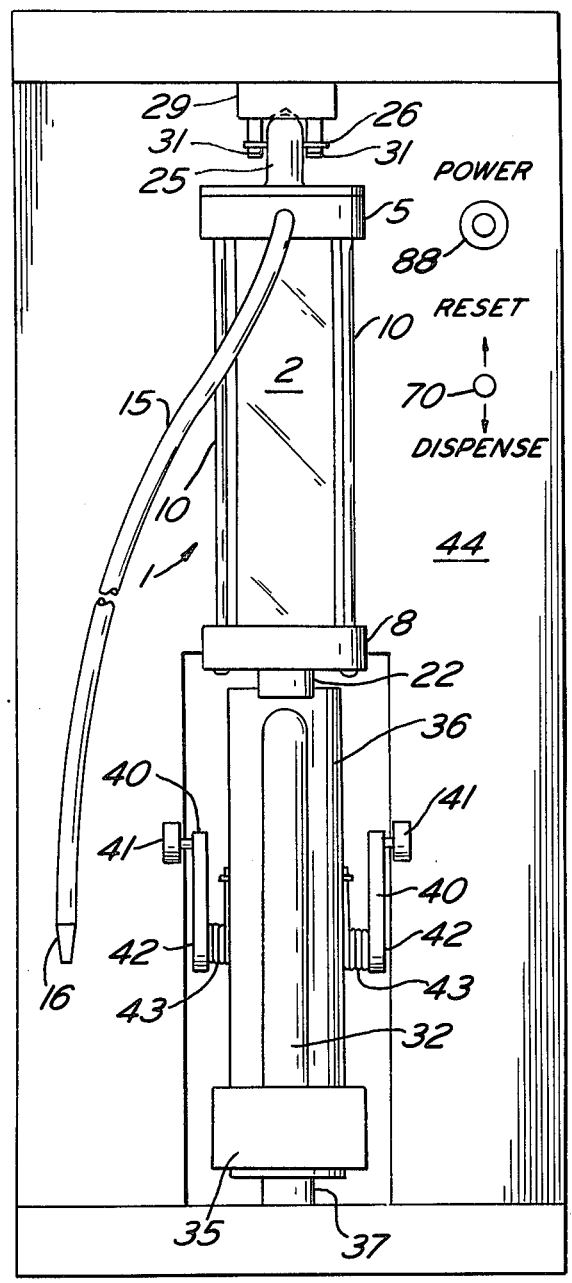
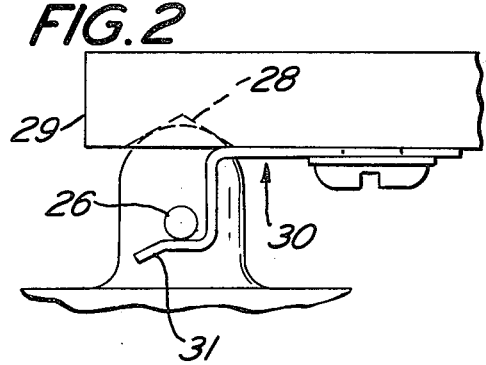
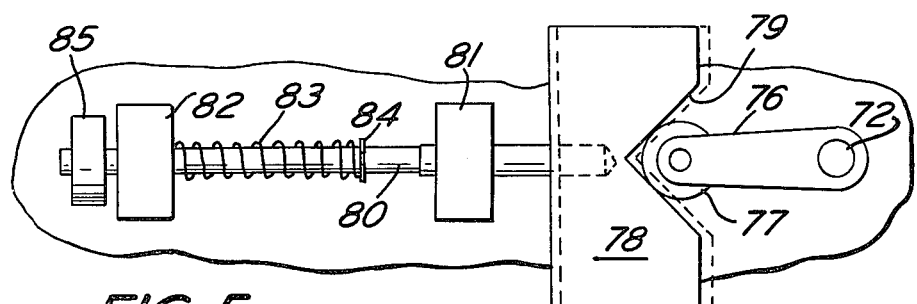

FIG. 6
FIG. 7
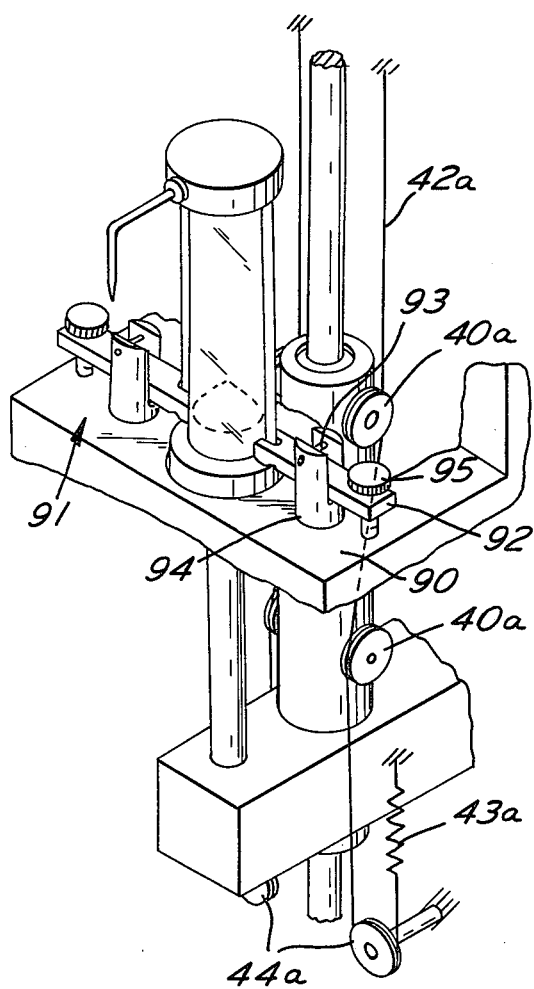
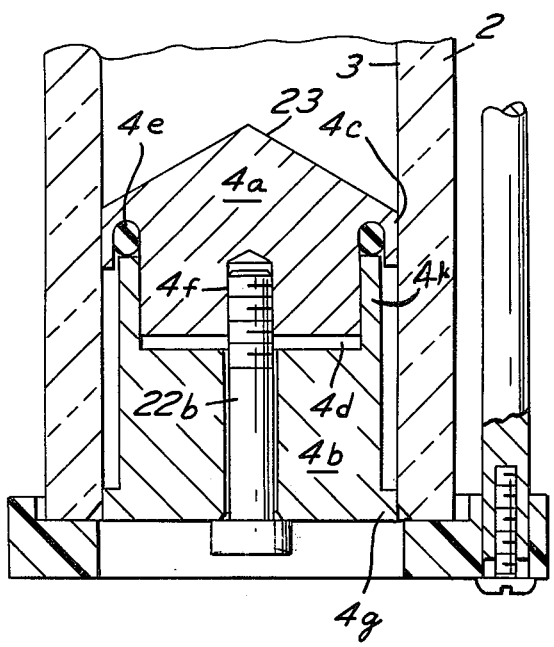

3,931,915

LIQUID-CONTAINING CARTRIDGE AND A DEVICE FOR DISPENSING MEASURED AMOUNT OF LIQUID FROM SUCH A CARTRIDGE

DESCRIPTION OF THE INVENTION

The present invention concerns a novel container or receptacle for a liquid, such as a reagent to be used for analytical purposes. When charged or filled with liquid, the filled container may be referred to herein as a package or cartridge. The container unit comprises a port at one end of the container through which a liquid may be introduced into or discharged from the container and a plunger or piston at the other end thereof adapted to be moved longitudinally within the container to displace liquid from a liquid-containing package made from the container and dispense it through the port. The invention also concerns means adapted to cooperate with such a liquid-containing package or cartridge to dispense liquid therefrom through the port in a manner such that spurting and splashing is practically avoided although the discharge of the liquid is effected rapidly.

It is an object of the invention to provide a novel container adapted to be charged with a liquid content at one location to provide a liquid-containing package or cartridge which can then be stored, refrigerated, and/or shipped or transported to another location where it may be used for its intended purpose.

Another object is to provide a device which is adapted to receive a package or cartridge of the type mentioned and has means for dispensing one or more measured amounts of liquid from the package.

Another object of the invention is to provide means for moving the piston within the container or cartridge in such a manner as to accelerate and decelerate from stopped positions at the beginning and end of the piston motion during dispensing so that splashing and spurting is avoided during the dispensing action.

Other objects and advantages will be apparent from the drawing and description hereof hereinafter.

In the drawing which is illustrative of the invention,

FIG. 1 is a side view, partly in section, of one embodiment of the container of the present invention, the container being disposed in an upright position and having a flexible dispensing conduit and nozzle attached, FIG. 2 is a side elevation showing in detail the arrangement for mounting or installing the package of FIG. 1 in a device for dispensing liquid from it, FIG. 3 is a front elevation of one embodiment of a device of the present invention adapted to dispense one or more accurately measured amount of liquid from a liquid-containing cartridge of FIG. 1, FIG. 4 is a perspective view of the essential mechanism for operating the device of FIG. 3, FIG. 5 is an enlarged plan view of null-positioning means, FIG. 6 is a perspective view showing a modification of the means for reducing play of the rod carriage and means for releasably mounting the container unit to the dispensing device, and FIG. 7 is an axial cross-sectional view of a modified container unit using a modified piston structure.

One embodiment of container or receptacle 1 of the present invention is shown in FIGS. 1 and 2. It comprises a tube 2 having a cylindrical inside wall 3 within which a plunger or piston 4 is movable longitudinally or axially. The length L of the piston wall is at least one-third as large as its diameter D (and is preferably much larger, such as at least as large as the diameter) to avoid any tendency of the unit to buckle upon insertion of the ramrod during dispensing. The tube 2 may be opaque or translucent, but is preferably transparent to facilitate observation of the liquid contents. It may be made of glass, metal, or rigid plastic material. The upper end of tube 2 fits within a recess in the head block 5 and is seated therein against a compressible resilient gasket 6. A resilient rubbery ring 7 fits in an annular recess in the wall of the piston and serves to seal the space between the plunger and the internal wall of tube 2. The O-ring 7 is in effect a dynamic low-friction seal which essentially eliminates leakage of the liquid along the piston wall during storage and also during operation to dispense liquid from the container. A base block 8 in the form of a ring has an internal annular seat 9 against which the lower end of tube 2 rests when the container is assembled as shown in FIG. 1 by fastening head 5 and base 8 together, as by tie-rods 10, thereby securely clamping the tube 2 between the head 5 and base 8. The inside diameter of the ring, as shown, is slightly larger than the internal diameter of the cylinder 3. This facilitates removal of the piston without disconnecting the tie-rods.

A split retaining ring 11 may be provided in a groove, as shown, in the inside wall of the base block ring 8 to hold a rubbery O-ring seal 12 in place behind the piston. This O-ring is resilient and serves as a spring to absorb any shifting of the piston 4 resulting from thermal expansion of the liquid during storage when the container is fully charged.

A passageway 13 extends from the inside face of head 5 (which serves as one end wall of the chamber of the container unit) to the exterior of head 5 e.g. the lateral periphery thereof. The latter end of the passageway may be tapped so that a threaded plug (not shown) may be inserted to close the container after insertion of the liquid contents and the piston 4. The filled container can then be stored, refrigerated or heated, and/or transported to another location for use in dispensing small doses of its contents.

The container unit 1 is adapted to be secured to a supporting element of a device for receiving the unit in a position wherein a ramrod may engage the piston and push it into the tube 2.

In the embodiment shown in FIGS. 1 to 3, means is provided on the head block 5 for securing the container unit 1 to a support and access means is also provided which serves (when the plug is replaced with a suitable fitting 14) to facilitate operation of the piston 4 to displace liquid within the chamber of the tube 2 and dispense it through the passageway 13 and the fitting 14 into a conduit 15 which terminates in a nozzle or tip 16 (FIG. 3), the conduit preferably being formed of a flexible tube, such as of rubber, Teflon, or the like. Conduit 15 may be secured, as by means of the threaded sleeve 17, to the nipple 18 of fitting 14 so that its passage communicates with passageway 13. A gasket 19 seals the junction of the tubing 15 and the end of nipple 18. Instead of plugging the external opening of passageway 13 for closing the container or package unit 1, the fitting 14 may be inserted and a cap (not shown) may be screwed onto the threaded nipple 18 using a gasket, if desired.

The access means referred to comprises the central opening 20 within the base ring 8 through which a suitable rod (designated 32 in FIG. 3) may enter the container or package unit and make operative contact with the exposed back (or bottom) wall of the piston 4 to push the piston within the tube 2 longitudinally thereof. This external wall or surface of the piston may be provided with means for centering the force of the push-rod relative to the axis of the piston. This means may simply be a conical or spherical recess 21 (centered with respect to the piston axis) either in the exposed piston wall itself or in the end surface of an extension 22 projecting from the back of the piston as shown in FIG. 1.

The head of the piston (i.e. its forward face or wall) may be flat, spherical, or conical, the latter being shown at 23 in FIG. 1. When it is conical, as shown, the inner end wall or face of head 5 is correspondingly recessed as at 24, so that the piston can fully displace the liquid from the cylindrical liquid-containing chamber in tube 2 of the package unit.

A modified form of piston is shown in FIG. 7. In this embodiment, the piston comprises two sections 4a and 4b having mating or telescoping extensions. The head 23 of the piston may be formed as previously mentioned in connection with the other embodiment. The head component or element 4a of the piston has an annular skirt or overhang 4c which has sliding engagement within the inside wall 3 of the tube 2. Concentrically within the skirt 4c is a cylindrical projection or plug constituting the male component of the assembled composite piston. The outer surface of this component fits slidably within the inside wall 4d of a socket or cup formed in the section 4b by an annular projection 4k extending axially from the outer periphery of the member 4b. An annular groove between the skirt and the main body of 4a is adapted to receive a resiliently flexible ring 4e of an elastomeric material, such as rubber or synthetic rubber. The width of the projection 4k from member 4b is less than the width of the annular groove as shown. A cap screw 22b is adapted to pass through a central bore in element 4b and is threaded at its end to engage threads within a concentric bore 4f in element 4a. Tightening the cap screw 22b serves to compress the ring 4e and thereby convert the piston into an integral unit. Adjacent its exposed end, element 4b has an enlarged ring, rim or flange 4g having an outside diameter which fits slidably within the inside wall 3 of the tube 2. The ramrod 32 is adapted to push against the head of the cap screw and thereby move the piston in the container unit. The ring 4g aids in assuring that the piston moves in strict axial motion. The distance from the farthest end of the skirt to the end of 4e farthest from the skirt is preferably at least one-third the diameter of the piston.

The components 4a and 4b may be made of either metal or plastic; preferably they are of nylon, Teflon (registered trademark) or the like. The skirt 4c is preferably formed of a resilient material so that, when not confined within the wall 3, its free end springs out to a larger diameter than the inside diameter of wall 3. It thus serves as means for sealing the space between the piston and wall 3. The resilient ring 4e aids in the sealing action since by tightening screw 22b, the ring is compressed in a direction axially of the piston which causes expansion of the ring radially of the piston and exerts a force causing the skirt to expand or press against the wall 3 more tightly, thereby exerting greater sealing effect.

The container or cartridge unit comprises means constructed or arranged to cooperate with means on a stationary support for releasably attaching the unit to the support, especially to a support member on a device for operating the piston in the dispensing of the liquid content of the cartridge. In the embodiment shown in FIG. 1 this means is provided by stud 25 projecting upwardly from the head 5 and having a pin 26 extending transversely therethrough and projecting a short distance from the periphery on both sides of the stud. Stud 25 may be formed integrally with the block 5 or it may be formed on a cap plate 27 (as shown in FIG. 1) that is fastened to the top of the headblock 5, as by screws or the tie rods 10.

The top of the stud 25 is rounded off, preferably to semispherical shape, so that it can be turned on the axis of pin 26 when it is inserted into any suitable recess, such as the conical recess 28 (FIG. 2) in any suitable support member 29. A pair of spring elements 30 disposed laterally of the recess on the support (see also FIG. 3) have free offset ends 31 which serve as hooks holding projecting ends of the pin 26 releasably when the container is mounted on the support.

Alternatively as shown in FIG. 6, the stud 25, pin 26, and cap plate 27, may be omitted from the head block 5 and the base block 8 of the unit may be releasably attached, as by simple clamps, to an annular seat in an opening in a horizontal plate 90 extending outwardly from the wall 44 at a level above the ramrod used in the dispensing device. The opening and the seat in the horizontal plate are concentric with the axis of the ramrod as will be described hereinafter. Two or more clamps 91 disposed on the plate around the periphery of the annular seat may be arranged to extend over the upper rim of the base block 8 so that after disposition of the container unit in engagement with the seat, the clamping elements 92 which pass under pins 93 of slotted posts 94 fixed to the plate 90, may be placed on the rim of the base block 8 and tightened, as by screws 95, to clamp the block in the seat. While the annular seat below the top surface of plate 90 may be omitted, it aids in locating the container unit in centered position above the ramrod. This type of container unit is preferred because of its simplicity of construction (no stud 25 or pin 26 being necessary) and because of the fact that it can be clamped in place in precise alignment with the ramrod.

The device for driving the piston in the liquid-filled container unit or cartridge shown in FIG. 1 to dispense its contents comprises a ramrod movable longitudinally, means for advancing the ramrod in one or more predetermined measured increments, means for retracting the rod, fixed support means (relative to which the ramrod is movable) constructed and arranged to receive the cartridge and locate it with its longitudinal axis in approximate alignment with the rod and with its piston in the path of advancement of the rod.

In FIGS. 3 and 4, the ramrod 32 is movable longitudinally, i.e. lengthwise, and its upper end (as viewed in these figures) is adapted to be raised into engagement with the recess 21 in the exposed end wall of the piston 4 or in the end of the piston projection 22. If desired, a flexible rubber sleeve extension 22a may be placed on the projection to aid guiding of rod 32 into centering alignment with the piston.

The means for driving the rod 32 comprises the screw 33 (FIG. 4) which cooperates with an internally threaded fitting 34 secured to an arm 35 to which the rod 32 is rigidly attached and from which the rod projects upwardly.

Guide means is provided on the arm 35 to aid the screw means in driving the rod 32 smoothly. This guide means comprises sleeve 36 rigidly secured to the arm 35 with its axis parallel to the rod 32. This sleeve is longitudinally movable on a stationary guide rod or guidepost 37 extending vertically from a base support which may be the bottom of the housing to an upper support which may be the top of the housing for the device, suitable linear bearing sleeves 38 being provided within the sleeve 36 if desired.

Resilient means is provided for reducing or eliminating "play" and reducing or eliminating binding of the screwdriving means and arm-carriage assembly. This means serves to apply a torque to the carriage assembly on an axis that is transverse to the axis of the screw (and of the rod) to offset at least partly the torque resulting from the resistance of the piston to the rod as the latter moves the piston into the container unit to discharge liquid therefrom. Any suitable means may be provided for exerting this torque on the arm-carriage assembly. In the embodiment shown in FIGS. 3 and 4 two arms 40 pivotally mounted on an axis 42 at right angles to that of sleeve 36 and provided with rollers 41 are biassed on their axis 42 by springs 43 so that the rollers bear against a vertical wall 44 (FIG. 3) which may be the front wall of the instrument casing and serve to relieve the binding tension or torque resulting from the pressure exerted by rod 32 against piston 4. Alternatively, the system diagrammatically shown in FIG. 6 may be used to exert this offsetting or counterbalancing torque. In this embodiment the tensioned arms 40 and elements 41, 42, and 43 are omitted. Instead, a pair of pulleys 40a are mounted on opposite sides of the sleeve 36 on a common axis perpendicular to that sleeve 36 and post 37 near the upper end of the sleeve as viewed in FIG. 6 and another similar pair of pulleys 44a are mounted on the opposite sides of the sleeve 36 on a common axis parallel to that of the first pair near the lower end of the sleeve. Two parallel cords or cables 42a are fastened at one of their ends, the top as shown, to a stationary member such as the ceiling or top of the housing for the device. The cords 42a are laced about the respective pulleys 40a and 44a in the manner shown in FIG. 6 and are connected at their other ends to respective springs 43a which are attached to a suitable fixed element adjacent their other ends so that the cords and springs are under tension at all times. If desired, the cords may be passed around additional pairs of pulleys, such as the pair of pulleys 44a shown, but these serve merely to allow a wider choice of the location of fixed elements to which the ends of the cords or springs may be fastened.

As stated hereinabove and shown in phantom dotted outline in FIG. 4, the cartridge of FIG. 1 is suspended from a fixed support 29 above the rod 32 so that the piston 4 in the cartridge is in alignment with the rod and advancing motion of the rod 32 longitudinally serves to push the piston further into the tube 2 of the container and thereby displaces a corresponding amount of liquid from the container through the attached conduit 15 having the tip or nozzle 16 which an operator can dispose above a suitable receptacle.

Limit switches 45 and 46 may be provided at the upper limit and lower limit of travel desired for ramrod 32 so that the upward motion of the ramrod will bring the piston 4 only to the upper inside end wall of the container unit and the downward motion of the ramrod 32 retracts it only to the desired extend below the cartridge to permit its removal. These switches are set in predetermined positions where they will be in the path of rod 32 or its carriage 35 or an element projecting therefrom. In FIG. 4, the member 47 attached to arm 35 serves to actuate these limit switches.

The screw 33 is driven by a pulley 48 secured to an extension 49 of the screw, the pulley 48 being driven by a timing belt 50 which in turn is driven by a pulley 51. The pulley 51 is secured to a slotted disc or wheel 52 for rotation therewith. While the member 52 is shown with a circular periphery broken only by the slot terminals, this slotted member may take the form of a Maltese cross, the typical driven element of a Geneva gear. Slotted member 52 is driven by the pins 53 of a driving pinwheel 54 secured to a shaft 55 which is connected by means of a flexible coupling 56 to a shaft 57 of a reversible electric motor 58.

FIG. 4 shows the various components in perspective and somewhat separated to aid in visualization. It is to be understood however that the members 52 and 54 constitute the driven and driving elements respectively of a modified Geneva gear type of mechanism. The driving element 54 in this particular embodiment has four pins 53 (located 90° apart on a common circle having the same axis as the shaft 55) extending laterally from the lower surface of the element so that, as one of these pins enters a slot of the driven element 52, another of the pins leaves an adjacent slot. The four slots in the element 52 extend radially inwardly from its outer circular periphery on lines 90° apart with respect to the axis of the shaft 59 on the axis of which element 52 rotates. Thus, the slot entrances are located on a circle concentric with the axis of shaft 59.

The shafts 49, 55, and 59 (and also shaft 72 hereinafter described) are mounted in suitable bearings disposed in fixed positions in suitable supports or framework in or on the housing of the device.

The circumference of the pulley 51 is four times the circumference of the pulley 48 driven by the belt 50 from pulley 51. Thus ¼ revolution of element 52 rotates the screw 33 a single revolution so that the rod 32 moves (upwardly for advancing the rod as shown in the particular embodiment) the distance corresponding to the pitch of the screw during the single revolution of the screw.

The driving action of element 54 having the pins 53 mounted thereon in cooperation with the element 52 provides a motion during a single revolution of the screw such that there is a gradual acceleration while a pin moves from its null position at the entrance to a slot to its greatest depth within the slot of element 52 where its motion is the most rapid and then a gradual deceleration until the position is reached in which the pin is ready to leave the slot and the next pin enters the next slot. This provides a type of motion of the rod 32 which gradually accelerates and then decelerates during each single revolution of the screw 33. This particular motion, which may be termed "quasi-sinusoidal", permits rapid discharge or dispensing action of the liquid from the nozzle or tip without causing spurting and splashing which normally accompanies the type of dispensing action in which there is sudden starting of the liquid discharge. Of course each of the pins 53 may be provided with a peripheral sleeve which is rotatable on the pin axis and thereby reduces the friction and wear that would be entailed by the motion of a fixed pin (without the sleeve within the slot of the element 52.

Means is provided for interrupting the advance of the ramrod 32 exactly at the end of a single revolution of screw 33 to precisely determine the amount of liquid dispensed during each such revolution. This means constitutes in effect a measuring means since the amount of liquid displaced by the motion of the rod 32 and the piston 4 determines the volume discharged upon a single revolution of the screw, the pitch of the screw being predetermined and the internal diameter of the cartridge chamber being also predetermined.

The means for precisely stopping the screw at the end of a revolution thereof comprises a disc 60 which is secured to the screw 33 concentrically for rotation therewith. This disc is provided with a notch 64 into which an index finger or rod 62 is adapted to project. The indexing element 62 constitutes one element of an electric relay. It extends into a stationary casing 63, a helical spring in the casing normally urging the index rod 62 against the disc periphery (and into the notch 64 when it comes into opposition) and is formed of magnetic material, such as soft iron, or has a magnetic component which extends into the sphere of influence of a solenoid coil 66. Secured to this finger 62 is a pin 67 which extends through a slot 68 in the casing 63. The electric switch which is closed by the operator when he actuates the DISPENSE switch 70 (FIG. 3) to dispense some of the liquid in the cartridge energizes the solenoid coil 66 thereby retracting index finger 62 from the position shown. The retraction causes pin 67 to close the switch 69 to cause operation of the reversible motor 58.

Means is provided to deenergize the solenoid 66 shortly after notch 64 has moved past the indexing member 62. This means comprises a cam 71 secured for rotation with shaft 72. This shaft has a pulley 73 fixed thereon for rotation therewith. Pinwheel 54 is formed with a circular periphery adapted to serve as a pulley. A timing belt 74 is driven by the peripheral surface of the pin element 54 and drives the pulley 73. The ratio of the periphery of 54 to that of 73 is 4 to 1 so that shaft 72 makes a single revolution while the screw 33 does so. The rise of cam 71 is set on shaft 72 so that switch 75 is closed at any point desired after notch 64 passes the retracted index finger 62. Closing of switch 75 actuates a relay to open the circuit through solenoid 66, thereby deenergizing it and allowing the spring to urge the finger 62 against the periphery of disc 60. The contacts of switch 69 remain closed until the finger 62 drops into notch 64, whereupon switch 69 opens and the current to the motor ceases. Entry of finger 62 into the notch 64, of course, serves to prevent any inertial tendency of the motor 58 to continue rotation of the screw 33 beyond a single revolution.

Means is provided for positioning the driving and driven members 54 and 52 of the Geneva gear at the termination of each "dose" delivery so that a pin 53 is exactly in the null position with respect to the entrance to slot in member 52 when the driving mechanism (including shafts 49, 55, 59 and 72) comes to a stop as determined by entrance of index rod 62 into notch 64. This means comprises an arm 76 which is secured to the shaft 72 for rotation therewith and carries at its end a cam follower roller 77. In the plane of the orbital path of roller 77, there is disposed a movable member 78. This member has a notch 79 and is fixed to rod 80 which extends through and is slidable in the fixed frame members 81 and 82. The center line of rod 80 runs through the vertex of the notch 79 (whose dihedral angle it bisects) and is in alignment with the line through the axes of shaft 72 and roller 77 when the index rod 62 is in notch 64. A helical spring 83 surrounds the rod 80, extending between the fixed frame member 82 and a collar 84 fixed on the rod 80, and urges the notched member 78 radially toward the axis of shaft 72 into its dotted line position (FIG. 5) wherein the collar 85 fixed to the end of rod 80 comes against the fixed member 82. Member 78 remains in the dotted line position until roller 77 comes into contact with it. The roller 77 rides into notch 79 on each revolution of the shaft 72 and forces member 78 into its solid line position shown in FIG. 5. Since the circumference of pinwheel pulley 54, about which belt 74 is driven, is four times the circumference of pulley 73, the follower 77 engages the notch 79 in the relative position shown in FIG. 5 each time one of the four pins 53 is exactly in its null position, i.e., at the entrance of a mating slot in the member 52. This occurs at the end of each revolution of the screw 33 since the circumference of pulley 51 is also four times that of pulley 48. Whenever the screw 33 is stopped at the end of a revolution thereof, at which time the index rod 62 engages notch 64 in disc 60, the engagement of the notch 79 by the roller 77 assures that the shaft 72 (if it should stop slightly before or after perfect alignment of arm 76 with notch 79) will be forced (by the configuration of the notch 79 cooperating with roller 77) into the exact position shown in FIG. 5 and this will serve to put the respective pin 53 in its exact null position relative to the entrance to the corresponding (mating) slot in member 52. This is important in order to avoid extremely high forces that would be exerted between the pin and slot in starting from a stopped position in which the pin is displaced appreciably from its null position exactly in the entrance to the groove. It is especially important when it is necessary to use a precisely designed modified Geneva gear type mechanism with minimum clearances and play in order to obtain precise movement of the piston 4. Since the use of the modified Geneva gear type of mechanism results in rotating the screw 33 at a varying rate, the pressure exerted by rod 32 on the piston 4 and then on the fluid discharged through the conduit 15 also varies in a way that alternately increases and decreases gradually in sinusoidal-like fashion.

Operation of the device described, should be apparent from the description hereinabove. Briefly the instrument is plugged into a suitable power line, e.g. the typical 110 volt AC electric line. The instrument may comprise a transformer to reduce the voltage to a voltage suitable for the motor 58.

After closing the master switch 88 (FIG. 3), the switch 70 is flipped to RESET position. This reverses rotation of the motor 58 and retracts the driving mechanism without interruption to the lower position of ramrod 32 as determined by limit switch 46, if the device is not already in such position. A cartridge 1 is inserted with its stud 25 into recess 28 of the overhanging support 29 and its transverse pin 26 hooked by springs 31. In this position, the unit 1 is suspended above rod 32 and can easily be swung so that the piston recess 21 is in alignment with the ramrod, the band 22a aiding this alignment. The plug is replaced with the fitting 14 and the nozzle-tipped conduit 15, and when ready for dispensing, the operator places tip 16 in or over a suitable receptacle, such as a test tube, vial, or the like, and flips switch 70 to DISPENSE position.

As stated previously this energizes solenoid 66, withdrawing index rod 62 from notch 64 to allow rotation of screw 33 and closes switch 69 which energizes motor 58 to drive it in "forward" mode, that is to rotate screw 33 in such a manner as to raise ramrod 32 against the piston. Since the upper end of rod 32 is not in engagement with the piston at first, and since conduit 15 and nozzle 16 may be empty to start with, it may be necessary to flip the DISPENSE switch one or more times before the nozzle 16 discharges liquid. The first dose discharged should be discarded as it may not represent a full-sized dose. After discard of one liquid discharge, the remaining doses are each of accurately predetermined size which is, of course, known from the pitch of screw 33, the diameter of the inside wall 3 of the container tube 2, and the shape of the piston head. The system is suitable for the dispensing even of small doses that are customarily used in microanalysis. For example, the pitch of screw 33 may be from about a fourth of a millimeter to one or more millimeters, a half-millimeter being a preferred size, the inside diameter 3 of the tube 2 being from about 5 to about 25 or more millimeters, and the slope of the piston head 23, if conical, may be from about 5° to 50°, preferably about 10° to 30°. The cartridge may be of a wide variety of sizes to contain, for example, from about one to several hundred millileters and the dispensing device may be capable of from about 10 to several hundred microliters as a single aliquot or dose.

While reference herein has been made to the packaging of liquid reagents, the invention is not limited to this particular use since the container unit and the dispensing device may be used for the packaging, storage, shipment, and dispensing of liquids of any other type for any purpose whatsoever.

It is to be understood that changes and variations may be made within the spirit and scope of the invention as defined in the appended claims.

We claim:

1. A packaging unit adapted to contain a liquid, adapted to be heated or refrigerated, if desired, and to serve as a storage receptacle from which one or more measured amounts of liquid may be dispensed from time to time, as desired, the unit comprising:
   a. a tube having an internal cylindrical wall,
   b. a head block at one end of the tube,
   c. a base block at the other end of the tube,
   d. means for clamping the tube endwise between the two blocks,
   e. a piston having a cylindrical peripheral wall extending along at least a portion of the length of the piston and fitting slidably in the internal cylindrical wall of the tube so that it is movable lengthwise in the tube, the piston having a back wall,
   f. means for sealing the space between the piston and the internal wall of the tube to prevent leakage during movement of the piston,
   g. the opposed inside walls of the headblock and the piston and the internal wall of the tube constituting the defining walls of a chamber in the unit adapted to receive a liquid therein,
   h. a passageway in the head-block having one end communicating with the chamber and the other end accessible to the outside of the unit, and
   i. the base block being in the form of a ring having a central opening and an internal annular seat for receiving said other end of the tube, the inside diameter of the ring being slightly larger than the internal diameter of the tube, said central opening providing access means in the base block adapted to permit insertion of a ramrod against the back wall of the piston to move the piston lengthwise of the tube, the ring having an inside groove, a split retaining ring in the groove, and a rubbery ring held in place by the retaining ring behind the piston.

2. A unit according to claim 1 in which the means (f) comprises a resilient annular skirt which is so constructed that its outer annular surface along its free edge normally presses resiliently against the internal wall of the tube.

3. A unit according to claim 2 in which the piston comprises two telescoping components, means for securing the components together, one of the components having a plug fitting slidably within a socket formed by an annular extension on the other component, an annular groove between the annular skirt and the plug in alignment with, and adapted to receive, the annular extension, a resilient ring fitting within the groove, the securing means being adjustable to cause the annular extension to press the resilient ring into the groove and thereby vary the pressure of the skirt against the internal wall of the tube.

4. A unit according to claim 3 in which the securing means comprises screw means passing through one component and engaging a threaded bore in the other.

5. A unit according to claim 1 in which the length of the piston wall is at least one-third its diameter.

6. A unit according to claim 1 comprising a removable closure for the accessible end of the passageway.

7. A unit according to claim 1 comprising means on the piston adapted to center a ramrod when the latter is inserted through the access means.

8. A device for dispensing one or more definite aliquots of liquid from a package unit consisting essentially of a hollow tube having a port at one end thereof and a piston within the tube, the piston having a forward wall, a back wall, and an outer cylindrical surface provided with an annular sealing means and fitting slidably within the inside wall of the tube whereby the piston is movable axially back and forth within the tube, and access means at the other end of the tube adapted to receive a ramrod in engagement with the back wall of the piston to move the piston axially within the tube to force liquid therein through the port, said device comprising a support, a ramrod movable lengthwise in either direction in a path extending between a retracted position and an advanced position, driving means for moving the ramrod lengthwise relative to the support selectively (a) to advance the ramrod in one or more increments toward its advanced position and (b) to retract it, means for releasably mounting the package unit on the support with its access means in the path of advance of the ramrod so that, on advance of the ramrod from its retracted position, it engages the back wall of the piston and pushes the piston further into the tube, thereby forcing liquid therein through the port, the driving means comprising means for accelerating the ramrod advance movement to a maximum and then decreasing the rate of such movement from start-to-end of each increment.

9. A device for dispensing one or more definite aliquots of liquid from a package unit consisting essentially of a hollow tube having a port at one end thereof and a piston within the tube, said piston having a forward wall, a back wall, and an outer cylindrical surface provided with an annular sealing means and fitting slidably within the inside wall of the tube whereby the piston is movable axially back and forth within the tube, and access means at the other end of the tube adapted to receive a ramrod in engagement with the back wall of the piston to move the piston axially within the tube to force liquid therein through the port, said device comprising a support, a carriage movable relative to the support, a ramrod secured to the carriage and projecting lengthwise therefrom in the direction of movement of the carriage, driving means for moving the carriage and thereby moving the ramrod lengthwise relative to the support to advance the ramrod in one or more increments between successive stationary positions of the ramrod, and means for predetermining the distance between successive stationary positions, the driving means comprising a rotatably mounted screw shaft, an internally threaded fitting fixed to the carriage in a position offset laterally from the ramrod and engaging the thread of the screw shaft and means for rotating the screw shaft through one revolution for each increment, said last-named means being constructed to impart an accelerating-decelerating rotation of the screw shaft during each revolution thereof, thereby accelerating the ramrod advance movement and then decreasing the rate of such movement from start-to-end of each increment.

10. A device for dispensing one or more definite aliquots of liquid from a tubular package unit having a discharge passage, a piston movable within the tube to force liquid in the unit through the passage, and access means adapted to receive a ramrod in back of the piston, said device comprising a stationary support, a rod, driving means for moving the rod lengthwise relative to the support, the support having mounting means thereon adapted to receive the package unit and support it with its access means in the path of advance of the rod, said driving means comprising a rotatable shaft having a screw thread thereon, a carriage having a threaded member engaging the screw thread, said rod being fixed to the carriage and extending parallel to the axis of the screw shaft, means for rotating the shaft in a direction to advance the rod lengthwise, and means for interrupting rotation of the screw shaft in a predetermined angular position relative to the support, the means for rotating the screw shaft comprising a modified Geneva gear type of mechanism having a four-pin driving member and a four-slot driven member, which during each revolution of the screw shaft, gradually increases the rate of rotation of the shaft from its starting position to a maximum and then gradually decreases the rate of rotation of such shaft to its stopped position.

11. A device according to claim 10 comprising means for assuring that on stopping, the next driving pin of the pinwheel is in the precise null position with respect to the cooperating slot of the driven member of the Geneva gear.

12. A device according to claim 11 wherein the means for interrupting rotation of the screw shaft comprises a concentric disc fixed on the screw shaft for rotation therewith, a notch in the periphery of the disc, an index member adjacent the disc periphery at a fixed angular position with respect to the disc, means for urging the member against the periphery of the disc and into the notch, to stop the screw shaft at a precise point in its revolution, means for withdrawing the index member from the notch when starting the next dispensing increment, and cam means for rendering the withdrawing means ineffective after the notch in the disc passes its position of opposition to the index member.

13. A device for dispensing a liquid in one or more aliquots of measured amount from a package unit having a liquid-containing tube, a port at one end of the tube in communication with the liquid in the tube, a piston within the tube, said piston having a forward wall, a back wall, and an outer cylindrical surface provided with an annular sealing means and fitting slidably within the inside wall of the tube whereby the piston is movable axially back and forth within the tube to force liquid within the tube through the port, and access means adapted to receive a ramrod in engagement with the back wall of the piston, said device comprising:
 a. a ramrod having a retracted position and an advanced position,
 b. means for releasably mounting the package unit with its access means in alignment with the ramrod in retracted position,
 c. means for incrementally advancing the ramrod lengthwise against the back wall of the piston, and thereby pushing the piston axially ahead of it in one or more increments toward said advanced position, comprising:
  1. a rotatable screw shaft mounted with its axis offset from and parallel to the ramrod,
  2. means comprising a reversible motor for rotating the screw shaft on its axis,
  3. means for interrupting rotation of the screw shaft at a predetermined angular position at the end of each revolution of the screw shaft whereby the size of each aliquot for a given piston depends on the pitch of the screw, and
  4. means for reversing the motor to move the ramrod to retracted position.

14. A dispensing device according to claim 13 wherein the driving connection between the motor and the screw shaft is so constructed and arranged that rotation of the shaft to move the ramrod toward its advanced position accelerates to a maximum and then decelerates from start-to-end of each revolution of the screw shaft.

15. A dispensing device according to claim 14 wherein the ramrod is secured to, for movement with, a carriage having a screw-threaded fitting engaging the screw of the screw shaft, the axis of the fitting and of the screw shaft being offset from the longitudinal axis of the ramrod.

16. A dispensing device according to claim 15 comprising a stationary guide member parallel to the screw shaft, and guide means of the carriage between the ramrod and the fitting thereon, and slidably engaging the guide member.

17. A device according to claim 16 comprising resilient means for applying a biasing torque to the carriage to offset at least partly the torque resulting from the resistance of the piston to the ramrod as the latter moves the piston into the package unit to discharge liquid therefrom.

* * * * *